(12) United States Patent
Peitz et al.

(10) Patent No.: US 12,274,975 B2
(45) Date of Patent: Apr. 15, 2025

(54) TWO-STAGE OFFGAS SCRUBBING

(71) Applicant: Evonik Oxeno GmbH & Co. KG, Marl (DE)

(72) Inventors: Stephan Peitz, Oer-Erkenschwick (DE); Guido Stochniol, Haltern am See (DE); Martin Oldemeyer, Haltern am See (DE); Matthias Böse, Raesfeld (DE)

(73) Assignee: Evonik Oxeno GmbH & Co. KG, Marl (DE)

( * ) Notice: Subject to any disclaimer, the term of this patent is extended or adjusted under 35 U.S.C. 154(b) by 698 days.

(21) Appl. No.: 17/560,226

(22) Filed: Dec. 22, 2021

(65) Prior Publication Data

US 2022/0226768 A1   Jul. 21, 2022

(30) Foreign Application Priority Data

Jan. 15, 2021   (EP) .................................. 21151735

(51) Int. Cl.
*B01D 53/02* (2006.01)
*B01D 53/14* (2006.01)
*C07C 51/12* (2006.01)
*C07C 51/44* (2006.01)

(52) U.S. Cl.
CPC ..... *B01D 53/1406* (2013.01); *B01D 53/1412* (2013.01); *B01D 53/1425* (2013.01); *B01D 53/1493* (2013.01); *C07C 51/12* (2013.01); *C07C 51/44* (2013.01); *B01D 2252/2021* (2013.01)

(58) Field of Classification Search
CPC ........ B01D 2252/2021; B01D 53/1406; B01D 53/1412; B01D 53/1425; B01D 53/1493; C07C 51/12; C07C 51/44; C11D 17/0004; C11D 17/0008; C11D 2111/20; C11D 7/261; C11D 7/5022
See application file for complete search history.

(56) References Cited

U.S. PATENT DOCUMENTS

| | | |
|---|---|---|
| 7,018,450 B2 | 3/2006 | Rojey et al. |
| 8,563,772 B2 | 10/2013 | Shaver |
| 9,856,184 B2 | 1/2018 | Stochniol et al. |
| 10,196,327 B2 | 2/2019 | Stochniol et al. |
| 10,633,302 B2 | 4/2020 | Nadolny et al. |
| 10,850,261 B2 | 12/2020 | Nadolny et al. |
| 10,882,027 B2 | 1/2021 | Nadolny et al. |
| 10,882,028 B2 | 1/2021 | Nadolny et al. |
| 11,186,782 B2 | 11/2021 | Peitz et al. |
| 2005/0215733 A1 | 9/2005 | Tsai et al. |

(Continued)

FOREIGN PATENT DOCUMENTS

CN   104 208 983 A   12/2014

OTHER PUBLICATIONS

European Search Report mailed on Jun. 14, 2021 in EP 21151735.4 (8 pages).

*Primary Examiner* — Christopher P Jones
(74) *Attorney, Agent, or Firm* — Grüneberg and Myers PLLC

(57) ABSTRACT

The invention provides a process for removing organic constituents from a gas stream in a two-stage scrubbing operation, in which scrubbing is performed firstly with an alcoholic scrubbing medium and then with an aqueous scrubbing medium. The laden scrubbing media obtained can be used in certain (chemical) processes.

20 Claims, 1 Drawing Sheet

(56) References Cited

U.S. PATENT DOCUMENTS

| | | | |
|---|---|---|---|
| 2010/0135885 A1* | 6/2010 | Patterson | B01D 53/1487 422/171 |
| 2019/0283004 A1 | 9/2019 | Nadolny et al. | |
| 2021/0053891 A1 | 2/2021 | Peitz et al. | |
| 2021/0053892 A1 | 2/2021 | Peitz et al. | |

* cited by examiner

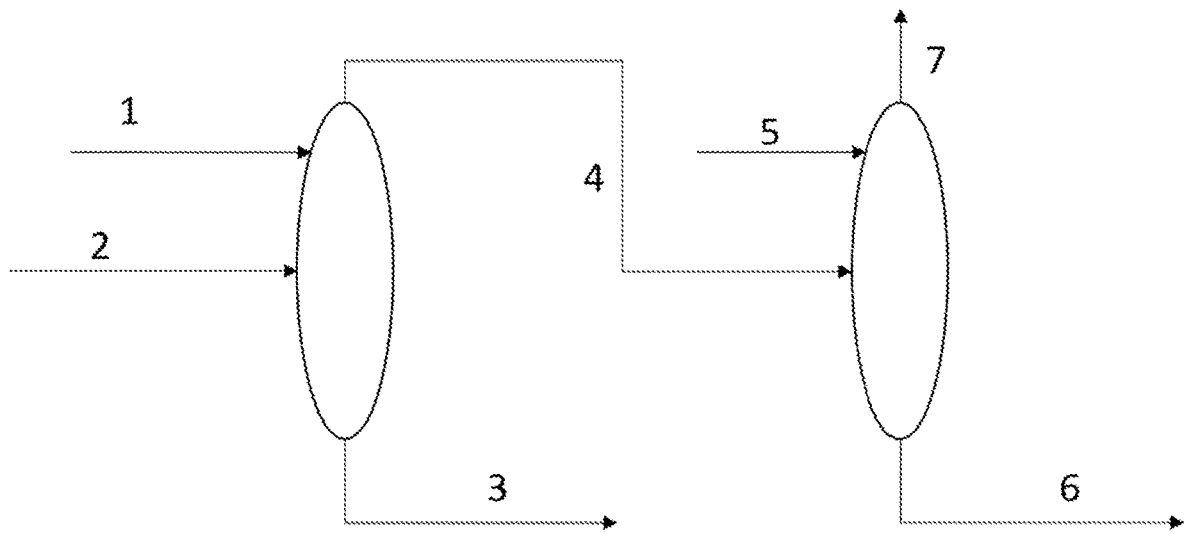

TWO-STAGE OFFGAS SCRUBBING

CROSS REFERENCE TO RELATED APPLICATIONS

This application is a 35 U.S.C. § 119 patent application which claims the benefit of European Application No. 21151735.4 filed Jan. 15, 2021, which is incorporated herein by reference in its entirety.

FIELD

The present invention relates to a process for removing organic constituents from a gas stream in a two-stage scrubbing operation, in which scrubbing is performed firstly with an alcoholic scrubbing medium and then with an aqueous scrubbing medium. The laden scrubbing media obtained can be used in certain (chemical) processes.

BACKGROUND

The chemical industry produces offgas streams at many points, for example when storing or filling feedstocks or products, such as offgases from tank blanketing or gases displaced when filling tank cars and railroad tank cars. These gas streams usually contain organic constituents which can originate from the stored or filled feedstocks. In order to comply with legal stipulations concerning emissions, these gas streams have to undergo an offgas scrubbing operation in order to scrub out the organic constituents that they contain.

The alcoholic and/or aqueous scrubbing media laden with the organic constituents are typically disposed of Such a disposal is not only expensive but also requires a comparatively high use of scrubbing medium. One option for circumventing this would be to work up the scrubbing media; however, this can be associated with high technical complexity.

SUMMARY

The object of the present invention was accordingly that of providing a simple and cost-effective process for removing organic constituents from a gas stream.

BRIEF DESCRIPTION OF THE DRAWINGS

FIG. 1 shows a schematic diagram of the process according to the invention

DETAILED DESCRIPTION

The object was achieved by the process described herein. The process according to the invention is a process for removing organic constituents from a gas stream in a two-stage scrubbing operation, wherein
the gas stream is scrubbed in a first scrubbing unit with a liquid alcoholic scrubbing medium, causing the organic constituents in the gas stream being cleaned to pass over at least partially into the scrubbing medium, and producing a gas stream with a reduced content of organic constituents, which contains some of the alcoholic scrubbing medium as alcoholic constituents, and an alcoholic scrubbing medium laden with organic constituents; and
the gas stream with a reduced content of organic constituents is scrubbed in a second scrubbing unit with an aqueous scrubbing medium, causing the alcoholic constituents to pass over at least partially into the scrubbing medium and producing a gas stream with a reduced content of organic and alcoholic constituents and an aqueous scrubbing medium laden with alcoholic constituents;
characterized in that in both scrubbing units in each case at least 0.7 kg of scrubbing medium is used per $m^3$ of gas stream being cleaned and at least 4 kg of scrubbing medium are used per kg of organic constituents to be removed, and in that
the alcoholic scrubbing medium laden with organic constituents is sent (back) into a (chemical) process in which the alcohol is used as a feedstock, and the aqueous scrubbing medium laden with alcoholic constituents is sent back into a (chemical) process in which the water is used as a feedstock or extractant.

The term "sent (back)" in the context of the present invention is to be understood as including both the situation in which the corresponding scrubbing medium can originate from a (chemical) process, into which it is sent back, and also the situation in which the corresponding scrubbing medium is provided freshly from a suitable vessel, and hence is provided without previously passing through a (chemical) process, but which after the scrubbing step is sent to a (chemical) process.

The term "(chemical) process" means both processes in which the corresponding scrubbing medium is used as a reactant and hence as a reaction partner and also processes in which it can be used as a further scrubbing medium or extractant.

With respect to the alcoholic scrubbing medium used in the first scrubbing step/in the first scrubbing unit, the (chemical) process into which the alcohol/the alcoholic scrubbing medium is sent (back) is a reaction in which alcohol is used as reactant. Examples of such processes include the production of ATBEs (alkyl tert-butyl ethers) or alkoxycarbonylation. It is apparent from the statements above that the terms alcohol and alcoholic scrubbing medium are used synonymously. In the case of methanol as possible alcoholic scrubbing medium, preferred (chemical) processes in which methanol is used as a reactant are an etherification (e.g. synthesis of MTBE=methyl tert-butyl ether or DME=dimethyl ether), a methoxycarbonylation or an esterification.

With respect to the aqueous scrubbing medium used in the second scrubbing step/in the second scrubbing unit, the (chemical) process is a process in which water is either the reaction partner or functions as a scrubbing medium or extractant. Preferred (chemical) processes in which the aqueous scrubbing medium, especially the water, is used are TBA synthesis (TBA=tert-butanol), hydrolysis and hydroxycarbonylation. Preferred (chemical) processes in which the aqueous scrubbing medium, especially the water, is used as scrubbing medium or extractant are ATBE synthesis, raffinate scrubbing or crack C4 hydrogenation. In each case, alcohols (ATBE synthesis) or polar contaminants (raffinate scrubbing, crack C4 hydrogenation) are removed with a water scrubbing.

The gas stream scrubbed in the process according to the invention and from which the organic constituents are removed is in particular organic-constituent-laden air or nitrogen which is obtained as offgas. Such offgas streams of air or nitrogen arise at many points in the chemical industry. In a preferred embodiment, the gas stream of air or nitrogen is obtained during storage or filling. In particular, the gas stream of air or nitrogen originates from vessels at least incompletely filled with liquid and is obtained as a result of displacement on filling, or originates from tanks in the filled state in which the gas stream is obtained during tank blanketing as a result of displacement of the gas cushion of tanks and vessels.

The organic constituents which in the process are scrubbed from the gas stream, and hence are present in the gas stream, may be a multitude of organic substances from the chemical industry. Examples of organic constituents are MTBE, ETBE, methanol, ethanol, C6 to C16 hydrocarbons, such as diisobutene, triisobutene, di-n-butene, dodecene, tetradecene, tetradecane, hexane, isooctane, 1-octene or decene, or mixtures thereof. The amounts present in the gas stream being cleaned preferably correspond to their vapor pressure at the corresponding storage or filling temperature, or possibly at ambient temperature.

The gas stream containing organic constituents in the process according to the invention in a first scrubbing unit is brought into contact with a liquid alcoholic scrubbing medium and thereby scrubbed. That is to say, the organic constituents in the gas stream being cleaned pass over at least partially into the scrubbing medium. This forms a gas stream with a reduced content of organic constituents, which now contains some of the alcoholic scrubbing medium as alcoholic constituents that have ended up in the gas stream as a result of the scrubbing, and an alcoholic scrubbing medium laden with organic constituents.

The first scrubbing unit is preferably a suitable column which ensures that the gas phase (the gas stream to be scrubbed) and the liquid phase (the alcoholic scrubbing medium) have sufficient contact with one another. Suitable for this purpose in particular is a column which has a contact zone comprising one or more structured packings or one or more random ring packings. The column used in the first scrubbing unit is preferably operated with a slight negative pressure of at most −30 mbarg (mbarg=millibar gauge). Such a negative pressure can be generated by a suitable pump, for example a water jet pump. The pump is preferably arranged downstream of the column, that is to say between the first and second scrubbing unit. The gas stream guided into the column can then be drawn to and out of the top of the column by the negative pressure generated.

The feed of the gas stream to the column of the first scrubbing unit is preferably arranged above the bottoms level of the column but below the contact zone. The feed for the liquid alcoholic scrubbing medium to the column of the first scrubbing unit, in contrast, is preferably arranged above the feed for the gas stream and above the contact zone. As a result, the gas stream to be scrubbed and the liquid alcoholic scrubbing medium can be brought into contact with each other in countercurrent in the contact zone, which in the present case ensures good scrubbing performance.

The temperature of the first scrubbing unit, in particular in the column of the first scrubbing unit, is variable in principle. In a preferred embodiment, the temperature in the first scrubbing unit corresponds to the respective ambient temperature.

The alcoholic scrubbing medium should be used in the first scrubbing unit in certain amounts in order to achieve a satisfactory scrubbing action. These amounts according to the invention are those in which at least 0.7 kg of alcoholic scrubbing medium, preferably at least 1.2 kg of alcoholic scrubbing medium, are used per $m^3$ of gas stream being cleaned and at least 4 kg of alcoholic scrubbing medium, preferably at least 8 kg of alcoholic scrubbing medium, are used per kg of organic constituents to be removed. In a particularly preferred embodiment, at least 1.5 kg of alcoholic scrubbing medium, more preferably at least 5 kg of alcoholic scrubbing medium, more preferably at least 7 kg of alcoholic scrubbing medium, particularly preferably at least 8 kg of alcoholic scrubbing medium, are used per $m^3$ of gas stream being cleaned. In a likewise preferred embodiment, at least 11 kg of alcoholic scrubbing medium, more preferably at least 15.5 kg of alcoholic scrubbing medium, particularly preferably at least 17 kg of alcoholic scrubbing medium, are used per kg of organic constituents to be removed.

As a result, the organic constituents in the gas stream being cleaned are removed from the gas stream being cleaned in particular to an extent of more than 90%, more preferably to an extent of more than 95%, more preferably to an extent of more than 98%, particularly preferably to an extent of more than 99%.

The alcoholic scrubbing medium which is used in the first scrubbing unit is especially an alcohol which is liquid at −10° C. The liquid alcoholic scrubbing medium is preferably a C1 to C4 alcohol, particularly preferably is methanol or ethanol. Methanol or ethanol are accordingly also preferred because this is relatively easy to integrate into a petrochemical integrated system in terms of plant and process technology. If the liquid alcoholic scrubbing medium is methanol, the methanol laden with the organic constituents from the gas stream according to the invention can be used for the production of MTBE. If the liquid alcoholic scrubbing medium is ethanol, the ethanol laden with the organic constituents from the gas stream according to the invention can be used for the production of ETBE. The organic constituents which have been removed from the gas stream are then discharged via the MTBE or ETBE production. The scrubbing medium laden with organic constituents contains at most 10% by weight of organics, preferably <8% by weight, particularly preferably <5% by weight. Such amounts are non-critical in the MTBE synthesis or ETBE synthesis, for example.

The gas stream containing the alcoholic constituents from the first scrubbing unit in the process according to the invention is brought into contact in a second scrubbing unit with a liquid aqueous scrubbing medium and thereby scrubbed. That is to say, the alcoholic constituents of the gas stream being cleaned pass over at least partially into the scrubbing medium. The alcoholic constituents that are removed in the second scrubbing step are composed predominantly of the alcoholic scrubbing medium of the first scrubbing step/of the first scrubbing unit. A gas stream with a reduced content of organic and alcoholic constituents and an aqueous scrubbing medium laden with alcoholic constituents are formed during the scrubbing in the second scrubbing unit. The aqueous scrubbing medium laden with alcoholic constituents can for example be guided to an extraction or a scrubbing within an MTBE synthesis in order there to scrub methanol from the raffinate streams.

The second scrubbing unit is preferably a suitable column in which it is ensured that the gas phase (the gas stream to be scrubbed) and the liquid phase (the aqueous scrubbing medium) in a second contact zone are in sufficient contact to scrub out the alcoholic constituents. Suitable to this end in particular is a column which in the second contact zone comprises one or more structured packings or one or more random ring packings. The column used in the second scrubbing unit is preferably operated at the respective ambient pressure. Special setups are therefore not required, though they could be used.

The feed of the gas stream to the column of the second scrubbing unit is preferably arranged above the bottoms level of the column, but below the second contact zone. The feed for the liquid aqueous scrubbing medium to the column of the second scrubbing unit is, in contrast, preferably arranged above the feed of the gas stream and above the second contact zone. As a result, the gas stream to be scrubbed and the liquid aqueous scrubbing medium can be brought into contact with each other in countercurrent in the second contact zone, which in the present case ensures good scrubbing performance.

The temperature of the second scrubbing unit, in particular in the column of the second scrubbing unit, is variable in principle. In a preferred embodiment, the temperature in the second scrubbing unit corresponds to the respective ambient temperature.

The aqueous scrubbing medium should be used in the second scrubbing unit in certain amounts in order to achieve a satisfactory scrubbing action. These amounts according to the invention are those in which at least 0.7 kg of aqueous scrubbing medium, preferably at least 1.2 kg of aqueous scrubbing medium, is used per $m^3$ of gas stream being cleaned and at least 4 kg of aqueous scrubbing medium, preferably at least 8 kg of aqueous scrubbing medium, are used per kg of alcoholic constituents to be removed. In a particularly preferred embodiment, at least 1.3 kg of aqueous scrubbing medium, particularly preferably at least 1.5 kg of aqueous scrubbing medium, are used per $m^3$ of gas stream being cleaned. In a likewise preferred embodiment, at least 9.5 kg of aqueous scrubbing medium, particularly preferably at least 10.5 kg of aqueous scrubbing medium, are used per kg of alcoholic constituents to be removed.

As a result, the alcoholic constituents in the gas stream being cleaned are removed from the gas stream being cleaned in particular to an extent of more than 90%, more preferably to an extent of more than 95%, more preferably to an extent of more than 98%, particularly preferably to an extent of more than 99%.

The aqueous scrubbing medium which is used in the second scrubbing unit can in principle be virtually any aqueous solution. Preferably, however, the aqueous scrubbing medium used in the second scrubbing unit is water. The water has a purity in particular of at least 99.9%. Should methanol be used as the alcoholic scrubbing medium, it is recommended that the water used contains at most 1000 ppm by weight, preferably at most 500 ppm by weight, more preferably at most 200 ppm by weight, particularly preferably at most 80 ppm by weight, of methanol. After being used in the second scrubbing unit, the water may contain at most 30% by weight, preferably <25% by weight, particularly preferably <20% by weight, of alcohol.

The gas stream with a reduced content of organic and alcoholic constituents which is obtained from the process according to the invention in particular contains not more than 600 mg of organic and alcoholic constituents per $m^3$ of gas, preferably not more than 400 mg of organic and alcoholic constituents per $m^3$ of gas, particularly preferably not more than 200 mg of organic and alcoholic constituents per $m^3$ of gas.

FIG. 1 shows a schematic diagram of the process according to the invention. The diagram does not show, for example, associated units such as pumps, heat exchangers, and the like. The gas stream (2) being cleaned is sent to the first scrubbing unit, where the alcoholic scrubbing medium (1) is supplied above the feed of the gas stream (2) being cleaned. As a result, the alcoholic scrubbing medium (1) is brought into contact with the gas stream (2) being cleaned. In the process, the organic constituents pass over into the alcoholic scrubbing medium (1) to a very substantial extent. The alcoholic scrubbing medium (3) laden with the organic constituents is then taken off from the first scrubbing unit via the bottom. The gas stream (4) with a reduced content of organic constituents, which contains some of the alcoholic scrubbing medium as alcoholic constituents, is then sent to the second scrubbing unit. There, it is brought into contact with the aqueous scrubbing medium (5) which is supplied above the gas stream (4). As a result, the alcoholic constituents are removed from the gas stream to a very substantial extent. A gas stream (7) with a reduced content of organic and alcoholic constituents is obtained at the top of the second scrubbing unit and an aqueous scrubbing medium (6) laden with alcoholic constituents is obtained in the bottom of the second scrubbing unit.

EXAMPLES

Example 1 (not According to the Invention)

In a two-stage scrubbing operation, 85 $m^3$/h of a 30° C. warm gas stream consisting of N2 and 39.6 kg/h of gaseous MTBE is fed into the first scrubbing unit below the contact zone (Sulzer M250.Y structured packing; packing bed: 5.9 m height and 200 mm diameter), while 50 kg/h of 20° C. warm, liquid MeOH is introduced above the contact zone. The gas stream taken off at the top of this first scrubbing column now contains 13 kg/h of gaseous MeOH and is guided into the second scrubbing unit, where it is injected below the contact zone present therein (Sulzer M250.Y structured packing; packing bed: 5.9 m height and 200 mm diameter). 20 kg/h of 25° C. warm, liquid water is introduced above this contact zone. At the top of this second scrubbing column, the remaining offgas is discharged, said offgas being 40° C. warm on account of the enthalpy of mixing of MeOH/water. With 87 $m^3$/h of gas stream, it contains approximately 4.7 kg/h of MTBE and 2 kg/h of MeOH. The removal rate is thus 88.1% for MTBE and 84.6% for MeOH. The MTBE-laden MeOH scrubbing stream is supplied to the MeOH input stream of an MTBE synthesis. The MeOH- and MTBE-laden scrubbing water is supplied to a water stream which is used in a C4/water scrubbing of the MTBE synthesis plant.

Example 2 (not According to the Invention)

In a two-stage scrubbing operation, 85 $m^3$/h of a 30° C. warm gas stream consisting of N2 and 39.6 kg/h of gaseous MTBE is fed into the first scrubbing unit below the contact zone (Sulzer M250.Y structured packing; packing bed: 5.9 m height and 200 mm diameter), while 50 kg/h of 20° C. warm, liquid MeOH is introduced above the contact zone. The gas stream taken off at the top of this first scrubbing column now contains 13 kg/h of gaseous MeOH and is guided into the second scrubbing unit, where it is injected below the contact zone present therein (Sulzer M250.Y structured packing; packing bed: 5.9 m height and 200 mm diameter). 150 kg/h of 25° C. warm, liquid water is introduced above this contact zone. At the top of this second scrubbing column, the remaining offgas is discharged, said offgas being 26.5° C. warm on account of the enthalpy of mixing of MeOH/water. With 78 $m^3$/h of gas stream, it contains approximately 4.7 kg/h of MTBE and 0.001 kg/h of MeOH. The removal rate is thus 88.1% for MTBE and >99.9% for MeOH. The MTBE-laden MeOH scrubbing stream is supplied to the MeOH input stream of an MTBE synthesis. The MeOH- and MTBE-laden scrubbing water is supplied to a water stream which is used in a C4/water scrubbing of the MTBE synthesis plant.

Example 3 (not According to the Invention)

In a two-stage scrubbing operation, 85 m³/h of a 30° C. warm gas stream consisting of $N_2$ and 39.6 kg/h of gaseous MTBE is fed into the first scrubbing unit below the contact zone (Sulzer M250.Y structured packing; packing bed: 5.9 m height and 200 mm diameter), while 750 kg/h of 20° C. warm, liquid MeOH is introduced above the contact zone. The gas stream taken off at the top of this first scrubbing column now contains 16.4 kg/h of gaseous MeOH and is guided into the second scrubbing unit, where it is injected below the contact zone present therein (Sulzer M250.Y structured packing; packing bed: 5.9 m height and 200 mm diameter). 20 kg/h of 25° C. warm, liquid water is introduced above this contact zone. At the top of this second scrubbing column, the remaining offgas is discharged, said offgas being 43° C. warm on account of the enthalpy of mixing of MeOH/water. With 92 m³/h of gas stream, it contains approximately 0.004 kg/h of MTBE and 3.4 kg/h of MeOH. The removal rate is thus >99.9% for MTBE and 79.3% for MeOH. The MTBE-laden MeOH scrubbing stream is supplied to the MeOH input stream of an MTBE synthesis. The MeOH- and MTBE-laden scrubbing water is supplied to a water stream which is used in a C4/water scrubbing of the MTBE synthesis plant.

Example 4 (According to the Invention)

In a two-stage scrubbing operation, 85 m³/h of a 30° C. warm gas stream consisting of N2 and 39.6 kg/h of gaseous MTBE is fed into the first scrubbing unit below the contact zone (Sulzer M250.Y structured packing; packing bed: 5.9 m height and 200 mm diameter), while 750 kg/h of 20° C. warm, liquid MeOH is introduced above the contact zone. The gas stream taken off at the top of this first scrubbing column now contains 16.4 kg/h of gaseous MeOH and is guided into the second scrubbing unit, where it is injected below the contact zone present therein (Sulzer M250.Y structured packing; packing bed: 5.9 m height and 200 mm diameter). 150 kg/h of 25° C. warm, liquid water is introduced above this contact zone. At the top of this second scrubbing column, the remaining offgas is discharged, said offgas being 31° C. warm on account of the enthalpy of mixing of MeOH/water. With 86 m³/h of gas stream, it contains approximately 0.004 kg/h of MTBE and 0.01 kg/h of MeOH. The removal rate is thus >99.9% for MTBE and >99.9% for MeOH. The sum total of MeOH and MTBE in the offgas is thus only 14 g/h according to the invention. The MTBE-laden MeOH scrubbing stream is supplied to the MeOH input stream of an MTBE synthesis. The MeOH- and MTBE-laden scrubbing water is supplied to a water stream which is used in a C4/water scrubbing of the MTBE synthesis plant.

The invention claimed is:

1. A process for removing organic constituents from a gas stream in a two-stage scrubbing operation, wherein
    the gas stream is scrubbed in a first scrubbing unit with a liquid alcoholic scrubbing medium, causing the organic constituents in the gas stream being scrubbed to pass over at least partially into the scrubbing medium, and producing a gas stream with a reduced content of organic constituents, which contains some of the alcoholic scrubbing medium as alcoholic constituents, and an alcoholic scrubbing medium laden with organic constituents; and
    the gas stream with a reduced content of organic constituents is scrubbed in a second scrubbing unit with an aqueous scrubbing medium, causing the alcoholic constituents to pass over at least partially into the scrubbing medium and producing a gas stream with a reduced content of organic and alcoholic constituents and an aqueous scrubbing medium laden with alcoholic constituents;
    wherein in both scrubbing units at least 0.7 kg of scrubbing medium is used per m³ of gas stream being scrubbed and at least 4 kg of scrubbing medium are used per kg of organic constituents to be removed, and in that
    the alcoholic scrubbing medium laden with organic constituents is sent to a reaction in which the alcohol is used as a reactant, and the aqueous scrubbing medium laden with alcoholic constituents is sent into a process in which the water is used as a feedstock or extractant.

2. The process according to claim 1, wherein the organic constituents in the gas stream being scrubbed pass over into the scrubbing medium in the first scrubbing unit to an extent of more than 90%.

3. The process according to claim 1, wherein the alcoholic constituents pass over into the scrubbing medium in the second scrubbing unit to an extent of more than 90%.

4. The process according to claim 1, wherein a chemical process into which the water is sent is selected from the group consisting of a TBA synthesis, a hydrolysis or a hydroxycarbonylation in which the water is a reactant, or the water is used in a process as scrubbing medium or extractant.

5. The process according to claim 1, wherein the process into which the alcohol is sent is a reaction in which methanol is used as a reactant.

6. The process according to claim 1, wherein the gas stream is organic-constituent-laden air or nitrogen from vessels which arises as a result of displacement during filling or as a result of displacement of a gas cushion of tanks and vessels.

7. The process according to claim 1, wherein the first scrubbing unit is operated with a slight negative pressure of at most −30 mbarg.

8. The process according to claim 1, wherein the liquid alcoholic scrubbing medium is an alcohol which is liquid at −10° C.

9. The process according to claim 8, wherein the liquid alcoholic scrubbing medium is a $C_1$ to $C_4$ alcohol.

10. The process according to claim 9, wherein the liquid alcoholic scrubbing medium is methanol or ethanol and the laden methanol or ethanol from the process is used for the production of MTBE or ETBE, resulting in the discharge of the organic constituents via the MTBE/ETBE production.

11. The process according to claim 1, wherein the second scrubbing unit is operated at ambient pressure.

12. The process according to claim 1, wherein the aqueous scrubbing medium laden with alcoholic constituents is formed and is guided to an extraction of an MTBE or ETBE synthesis in order to scrub methanol or ethanol from a raffinate stream.

13. The process according to claim 1, wherein the water used contains at most 1000 ppm by weight of methanol.

14. The process according to claim 1, wherein the alcoholic constituents which are removed in the second scrubbing step consist of the alcoholic scrubbing medium of the first scrubbing step.

15. The process according to claim 1, wherein the gas stream with a reduced content of organic and alcoholic constituents contains not more than 300 mg of organic and alcoholic constituents per m³ of gas.

16. The process according to claim 1, wherein the water used contains at most 200 ppm by weight of methanol.

17. The process according to claim 1, wherein the gas stream with a reduced content of organic and alcoholic constituents contains not more than 100 mg of organic and alcoholic constituents per $m^3$ of gas.

18. The process according to claim 8, wherein the liquid alcoholic scrubbing medium is methanol or ethanol.

19. The process according to claim 1, wherein the alcoholic constituents pass over into the scrubbing medium in the second scrubbing unit to an extent of more than 95%.

20. The process according to claim 1, wherein the organic constituents in the gas stream being scrubbed pass over into the scrubbing medium in the first scrubbing unit to an extent of more than 98%.

* * * * *